(12) United States Patent
Bush et al.

(10) Patent No.: US 7,507,554 B2
(45) Date of Patent: *Mar. 24, 2009

(54) PROCESS FOR THE PRODUCTION OF ETHANOL FROM ALGAE

(75) Inventors: Ronnie A. Bush, Germantown, TN (US); Kevin M. Hall, Mesquite, TX (US)

(73) Assignee: Propulsion Logic, LLC, Germantown, TN (US)

( * ) Notice: Subject to any disclaimer, the term of this patent is extended or adjusted under 35 U.S.C. 154(b) by 291 days.

This patent is subject to a terminal disclaimer.

(21) Appl. No.: 11/435,992

(22) Filed: May 17, 2006

(65) Prior Publication Data

US 2007/0202582 A1    Aug. 30, 2007

Related U.S. Application Data

(63) Continuation-in-part of application No. 11/363,675, filed on Feb. 28, 2006, now Pat. No. 7,135,308.

(51) Int. Cl.
*C12P 7/39* (2006.01)
*C12P 7/14* (2006.01)
*C12N 1/12* (2006.01)
*C12N 1/16* (2006.01)

(52) U.S. Cl. .................. 435/42; 435/161; 435/162; 435/255.2; 435/257.1; 435/942; 435/946

(58) Field of Classification Search .................. None
See application file for complete search history.

(56) References Cited

U.S. PATENT DOCUMENTS

| | | | |
|---|---|---|---|
| 4,326,036 A | 4/1982 | Hayes | |
| 5,578,472 A | 11/1996 | Ueda et al. | |
| 7,135,308 B1 * | 11/2006 | Bush et al. | 435/42 |

* cited by examiner

*Primary Examiner*—Herbert J. Lilling
(74) *Attorney, Agent, or Firm*—Vance Intellectual Property, PC

(57) ABSTRACT

The present invention describes a process for the production of ethanol by harvesting starch-accumulating filament-forming or colony-forming algae to form a biomass, initiating cellular decay of the biomass, fermenting the biomass in the presence of a yeast, and the isolating the ethanol produced. The present invention further relates to processing of the biomass remaining after ethanol production to recovering biodiesel starting materials and/or generation of heat and carbon dioxide via combustion.

22 Claims, No Drawings

PROCESS FOR THE PRODUCTION OF ETHANOL FROM ALGAE

CROSS-REFERENCE TO RELATED APPLICATIONS

The present application is a Continuation-In-Part and claims the priority benefit of U.S. application Ser. No. 11/363,675, filed Feb. 28, 2006 now U.S. Pat. No. 7,135,308, which is expressly incorporated herein by reference.

FIELD OF THE INVENTION

This invention relates generally to a process for the production of ethanol by harvesting starch-accumulating filament-forming or colony-forming algae, initiating cellular decay, fermenting, and isolating the produced ethanol. The present invention further relates to forming biodiesel and/or generating heat and/or carbon dioxide from the biomass remaining after ethanol production.

BACKGROUND OF THE INVENTION

Ethanol is becoming an increasingly important alternative fuel as oil prices continue to rise in the wake of political instability and as new drivers come online in countries such as China and India. Corn, due to its fermentable sugars (e.g., carbohydrates), is currently an industrial starting material for ethanol.

U.S. Pat. No. 5,578,472 (U.S. Pat. No. '472) describes a different source of fermentable sugars, single-cell free floating algae. This patent discusses how single-cell free floating algae contain carbohydrates in their cells and can be cultured under laboratory conditions as a source of fermentable carbohydrates. The main drawback is that the process of U.S. Pat. No. '472 is not industrially scalable due to the inherent limitations of single-cell free floating algae.

In view of the above, it is desirable to find an alternative source of fermentable carbohydrates that can be used on an industrial scale.

SUMMARY OF THE INVENTION

Accordingly, the present invention provides a novel process of producing ethanol from starch-accumulating filament-forming or colony-forming algae.

The present invention further provides a novel process of producing biodiesel from the biomass remaining after ethanol production.

These and other objects, which will become apparent during the following detailed description, have been achieved by the inventors' discovery that starch-accumulating filament-forming or colony-forming algae can be effectively harvested, decayed, and fermented to form ethanol.

DETAILED DESCRIPTION OF PREFERRED EMBODIMENTS

Thus, in an embodiment, the present invention provides a novel process for forming ethanol from algae, comprising:
 (a) growing starch-accumulating, filament-forming or colony-forming algae in an aqua culture environment;
 (b) harvesting the grown algae to form a biomass;
 (c) initiating decay of the biomass;
 (d) contacting the decaying biomass with a yeast capable of fermenting it to form a fermentation solution; and,
 (e) separating the resulting ethanol from the fermentation solution.

Examples of the starch-accumulating filament-forming or colony-forming algae include an algae in a phylum selected from Zygnemataceae, Cladophoraceae, Oedogoniales, Ulvophyceae, Charophyceae, or a combination thereof. Examples of the starch-accumulating filament-forming or colony-forming algae include an algae selected from spirogyra, cladophora, oedogonium, or a combination thereof.

Aqua culture is a known way of farming in a water environment. Typically, the aqua culture is a controlled environment wherein addition and removal of materials (e.g., water) is controlled by the operator. Examples of aqua culture include, but are not limited to, ditches, troughs, oval races, and ponds (e.g., man-made ponds). The depth of the aqua culture is generally kept at 4 feet or less (e.g., 1, 2, 3, or 4 feet). The width and length of the structure (e.g., trench) can be as narrow or wide and short or long as desired and will often depend on the topography of the land. It is difficult for the light needed for algae photosynthesis to penetrate deeper than four feet. Mechanical devices for water flow (e.g., motorized paddles) can be present to enhance the water environment. Aqua culture is generally conducted in the open (i.e., the water environment is exposed to natural light and atmosphere). The water used for aqua culture is typically water from a natural source (e.g., river, lake, or well). It can be desirable to conduct the aqua culture on one or more acre-feet of water (e.g., 1, 2, 3, 4, 5, 6, 7, 8, 9, 10, or more acre-feet). A controlled environment can be helpful in preventing the release of waste or pollutants. The aqua culture system is a eutrophic environment wherein nutrients (e.g., phosphates and nitrates) are present in levels sufficient to promote rapid growth of the algae present. Examples of phosphate sources include, but are not limited to animal waste such as hog waste and/or poultry waste.

Growing, as used herein, means that the algae are kept in an aqua environment under conditions (e.g., phosphate levels, nitrate levels, and carbon dioxide levels) such that the algae increases in size with the goal of forming an algal bloom. An algal bloom is often a carpet-like structure of algae filaments or colonies that forms or floats on or near the surface of the aqua environment. The starch-accumulating, filament-forming or colony-forming algae used in the present invention generally can grow in the presence of atmospheric carbon dioxide. It can, however, be desirable to increase the level of carbon dioxide in order to enhance the growth of the algae. Carbon dioxide can be introduced via methods known to those of skill in the art (e.g., bubbling carbon dioxide into the aqua environment). As noted below, carbon dioxide obtained from the present invention can beneficially be used (e.g., recycled) to aid in the growth of the algae.

Harvesting, as used herein, is the act of collecting the grown algae (e.g., algal bloom). Generally harvesting is accomplished mechanically (e.g., raking, netting, dredging) and can be accomplished manually or automatically. The harvested algae are called a biomass.

Initiating decay, as used herein, means that the biomass is treated in such a way that the cellular structure of the biomass begins to decay (e.g., cell wall rupture) and release the carbohydrates contained therein. Initiating decay can be accomplished mechanically, non-mechanically, or a combination thereof. Mechanical initiation means that the biomass is subjected to some sort of mechanical distortion that begins the decay process. Examples of mechanical initiation include stirring, chopping, crushing, blending, grinding, extruding, and shredding. For example, the biomass can be placed into a vessel and blended. An desirably endpoint of the mechanical initiation can be when the biomass is emulsified. The mechanical initiation can be performed (a) under ambient light and atmosphere, (b) in the dark under an ambient atmosphere, and (c) in the dark and under anaerobic conditions (see below). Non-mechanical initiation means that biomass is placed in an environment where the presence of light and oxygen is limited or entirely absent so as to initiate and promote the decay of the biomass (e.g., a dark and anaerobic environment). The amount of light present will typically be so low that photosynthesis cannot continue. For example, the biomass can be placed in water under cover (e.g., inside a tank) where sunlight is prevented from contacting the biomass. Also, a gas (e.g., carbon dioxide or nitrogen) can be bubbled through the biomass and water to reduce or remove the presence of air. The cellular structure of the biomass under dark and anaerobic conditions is expected to begin to decay (e.g., cell wall rupture) and release the carbohydrates contained therein. This decay can occur without mechanical assistance, though mechanical assistance as described above can also be used. As an example, the biomass can be maintained under decay conditions for 1, 2, 3, 4, 5, 6, 7, or more days. The vessel, structure, etc. housing the biomass under decay conditions can be fitted with a sensor (or sensors) that will allow for sampling of the biomass to determine its level of decay. The sampling can be done by methods known to those of skill in the art to show when the cell walls of the algae have ruptured or are rupturing. For example, a sample of the biomass can be observed under a microscope to determine if the desired cell wall rupturing has been achieved. It can be desirable to wait until cell wall rupturing is observed before contacting the biomass with the fermentation yeast.

One of ordinary skill in the art would recognize that the quantity of yeast to be contacted with the biomass will depend on the quantity of the biomass present as well as the rate of fermentation desired. The yeasts used are typically brewers' yeasts. Examples of yeast capable of fermenting the decaying biomass include, but are not limited to, *Saccharomyces cerevisiae* and *Saccharomyces uvarum*. Besides yeast, genetically altered bacteria know to those of skill in the art to be useful for fermentation can also be used. The fermenting of the biomass is conducted under standard fermenting conditions.

Separating of the ethanol from the fermentation solution means that once ethanol begins to form from fermentation, it is then isolated from the fermentation solution. It is expected that the fermentation solution would contain at least water, ethanol, and the remaining biomass. Separation can be achieved by any known method (e.g. distillation). The separation operation can be performed on the liquid and solid portions of the fermentation solution (e.g., distilling the solid and liquid portions), or the separation can just be performed on the liquid portion of the fermentation solution (e.g., the solid portion is removed prior to distillation). In addition, separation of ethanol can be performed on an entire batch of fermentation solution. Alternatively, separating can entail removing the fermentation solution portion-wise (e.g., 1, 2, 3, 4, 5, 6, 7, 8, 9, 10, 20, 30, 40, 50% or more of the solution at a time) or continuously and replacing it with additional fermentation solution or liquid (e.g., water). The separated ethanol, which will generally not be fuel-grade, can be concentrated to fuel grade (e.g., at least 95% ethanol by volume) via methods known to those of skill in the art (e.g., a second distillation).

One of ordinary skill in the art recognizes that the level of ethanol present in the fermentation solution can negatively affect the yeast/bacteria. For example, if 17% by volume or more ethanol is present, then it will likely begin causing the yeast/bacteria to die. It can therefore be desirable to begin separating ethanol from the fermentation solution before or at least when ethanol levels of 12, 13, 14, 15, 16, to 17% by volume (ethanol to water) are observed. Ethanol levels can be determined using methods known to those of ordinary skill in the art.

The fermentation reaction can be run 1, 2, 3, or more times on the biomass. For example, once the level of ethanol in the initial (i.e., first) fermentation solution reaches 12-17% by volume, the entire liquid portion of the fermentation solution can be separated from the biomass or the fermentation solution in total (i.e., biomass and liquid portion) can be run through a procedure to isolate the ethanol (e.g., distillation). The once-fermented biomass can then be contacted with water and yeast/bacteria to form a second, third, etc. fermentation solution. This process can be repeated until the yield of ethanol is undesirably low. Typically, after the first fermentation run, the amount of biomass remaining in the vessel holding the biomass (e.g., tank) is determined. If less than half of the starting biomass remains, then it is assayed for carbohydrate level. If sufficient carbohydrates remain, then additional biomass is added and the fermentation process repeated. If sufficient carbohydrates do not remain, then the biomass is removed (e.g., pumped) from the vessel for further processing.

It can be desirable to isolate or harvest the yeast/bacteria from the fermentation reaction for recycling. The method of harvesting will depend upon the type of yeast/bacteria. If the yeast/bacteria are top-fermenting, then it can be skimmed off the fermentation solution. If they are bottom-fermenting, then it can be removed from the bottom of the tank.

A by-product of fermentation is carbon dioxide. During the fermentation process, it is expected that about one-half of the decomposed starch will be discharged as carbon dioxide. This carbon dioxide can be collected by methods known to those of skill in the art (e.g., a floating roof type gas holder). The collected gas can then be beneficially supplied to the algae aqua culture as an inorganic carbon source for growing the algae.

Lipids/oils, which are useful for forming biodiesel typically, remain in the biomass after it has been subjected to fermentation, and the fermentation solution has been removed. These lipids/oils can be isolated from the biomass and then used to form biodiesel using methods known to form biodiesel. A convenient method of separating lipids/oils from the biomass is by pressure. For example, the biomass can be pressed and the resulting lipid-rich liquid separated.

Thus, in another embodiment, the present invention provides a novel process for forming biodiesel starting materials, comprising: recovering the lipids/oils remaining in the biomass after fermentation and ethanol separating. This process can further comprise: converting the recovered lipids/oils into biodiesel.

The biomass recovered after fermentation (and possibly lipids/oils separation) contains stored energy that can be released via combustion. The process of combusting the biomass should provide heat that can be used to power the production of ethanol (e.g., distillation) (and/or isolation and processing of lipids/oils). The carbon dioxide released can also be recycled by capturing it and using it in the aqua culture environment to aid in growing the algae. As an example, the biomass remaining after fermentation and possibly lipids/oils separation can be air dried (or even oven dried if desired), formed (e.g., compressed) into a transportable unit (e.g., block or brick), and then burned. Ash remaining from the combustion can be used as nutrients for a new algae crop.

Starch-accumulating, filament-forming or colony-forming algae are known to bloom naturally in natural water sites (e.g., lakes, ponds, etc.) as well as in non-natural water sites (e.g., man-made lakes, ponds, reservoirs, etc.). Natural bloom, as used herein, covers all blooms that result from other than growing in an aqua culture environment as described above. Such blooms can threaten other native plant species as well as fish stocks. These blooms are a natural source (in contrast to the non-natural source described above) of starch-accumulating, filament-forming or colony-forming algae and can be used in the present invention. Therefore, the present invention also provides a novel process, comprising:

(a) harvesting a natural bloom of starch-accumulating, filament-forming or colony-forming algae to form a biomass;
(b) initiating decay of the biomass;
(c) contacting the decaying biomass with a yeast capable of fermenting it to form a fermentation solution; and,
(d) separating the resulting ethanol from the fermentation solution.

The remainder of the above discussion also applies to forming ethanol from a naturally-occurring bloom.

The present invention may be embodied in other specific forms without departing from the spirit or essential attributes thereof. This invention encompasses all combinations of aspects and examples of the invention noted herein. It is understood that any and all embodiments of the present invention may be taken in conjunction with any other embodiment or embodiments (or examples) to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

EXAMPLES

Example 1

The following description is a typical example of the present invention.

1. Trenches for ethanol production are built that are approximately 3-5 feet deep, 10-40 feet wide, and 100-200 feet long.
2. Water is pumped into the trenches or ponds from a natural (untreated) water source.
3. The water is sampled for nutrient levels and then nutrients (phosphates and nitrates) are added to bring the water conditions to a eutrophic condition for algae growth.
4. Spirogyra is then added to the nutrient rich water.
5. The water is monitored for about 2-4 weeks for algae growth rate and nutrient levels.
6. When the Spirogyra reach bloom conditions, the bloom is raked out of the trenches or ponds. Some Spirogyra are left in the water for the next crop.
7. The harvested algae (now called biomass) is placed in a sealed tank with enough water to just cover the biomass and allowed to set until enough biomass has been harvested to fill the tank.
8. Once the tank is full, air is pumped out of the tank and the contents are allowed to set for approximately 7 days.
9. A sample of the biomass is removed from the tank and examined under a microscope to determine if there is cell degradation.
10. When the cells have begun to degrade, *Saccharamyces Cerevisiae* yeast is added to the biomass to begin fermentation.
11. The fermentation process is monitored for the level of ethanol in the biomass liquid. This is done by removing a sample from the tank via a tap in the tank.
12. When the liquid has reached a level of 12% to 14% ethanol, the liquid is drained from the tank and pumped to a holding tank to be fed to a distillation unit.
13. The amount of biomass in the tank is checked. If it is below ½ of the starting amount, the remaining biomass is sampled for remaining carbohydrates.
14. If there are sufficient remaining carbohydrates, more biomass can be added to the tank for another cycle of degradation and fermentation.
15. If there are not sufficient remaining carbohydrates, the remaining biomass is pumped out of the tank.
16. Yeast from the fermentation cycle is harvested from the tank to be used in the next fermentation cycle.
17. The biomass from the tank is run thru a press to force out any lipids/oils remaining in the biomass.
18. The oils are then processed into biodiesel.
19. The biomass remaining after pressing is allowed to air dry.
20. The dried biomass is compressed into bricks.
21. The compressed, dried biomass is burned to provide heat for the ethanol distillation.
22. The ash remaining from the burned dried biomass is fed back into the trenches/ponds to feed a new generation of algal growth.
23. The ethanol production process can be repeated with a new algae crop to harvest on average (depending on water temperature and water quality) every two to four weeks.

Example 2

The following description is another typical example of the present invention.

1. Trenches for ethanol production are built that are approximately 3 feet deep, 5 feet wide, and 100 feet long.
2. Water is pumped into the trenches or ponds from a natural (untreated) water source.
3. The water is sampled for nutrient levels and then nutrients (phosphates and nitrates) are added to bring the water conditions to a eutrophic condition for algae growth.
4. Spirogyra is then added to the nutrient rich water.
5. The water is monitored for about 2-4 weeks for algae growth rate and nutrient levels.
6. When the Spirogyra reach bloom conditions, the bloom is raked out of the trenches or ponds. Some Spirogyra are left in the water for the next crop.
7. The harvested algae is now called biomass.
8. The biomass is blended to form an emulsion.
9. The blended biomass is pumped into a holding tank and yeast is added to the biomass to begin fermentation.
10. The fermentation process is monitored for the level of ethanol in the biomass liquid. This is done by removing a sample from the tank via a tap in the tank.
11. When the biomass has reached a level of 12% to 14% ethanol, the biomass is drained from the tank to be fed to a distillation unit.
12. If there are sufficient remaining carbohydrates, more biomass can be added to the tank for another cycle of degradation and fermentation.
13. If there are not sufficient remaining carbohydrates, the remaining biomass is pumped out of the tank.
14. Yeast from the fermentation cycle is harvested from the tank to be used in the next fermentation cycle.

15. The biomass from the tank is run thru a press to force out any lipids/oils remaining in the biomass.
16. The oils are then processed into biodiesel.
17. The biomass remaining after pressing is allowed to air dry.
18. The dried biomass is compressed into bricks.
19. The compressed, dried biomass is burned to provide heat for the ethanol distillation.
20. The ash remaining from the burned dried biomass is fed back into the trenches/ponds to feed a new generation of algal growth.
21. The ethanol production process can be repeated with a new algae crop to harvest on average (depending on water temperature and water quality) every two to four weeks.

Numerous modifications and variations of the present invention are possible in light of the above teachings. It is therefore to be understood that within the scope of the appended claims, the invention may be practiced otherwise that as specifically described herein.

What is claimed is:

1. A process for forming ethanol from algae, comprising:
   (a) growing starch-accumulating, filament-forming or colony-forming algae in an aqua culture environment;
   (b) harvesting the grown algae to form a biomass;
   (c) initiating decay of the biomass;
   (d) contacting the decaying biomass with a yeast capable of fermenting it to form a fermentation solution; and,
   (e) separating the resulting ethanol from the fermentation solution.
2. The process of claim 1, wherein the decay is initiated mechanically.
3. The process of claim 2, wherein the decay is initiated by placing the biomass in a dark and anaerobic aqua environment.
4. The process of claim 1, wherein the starch-accumulating filament-forming or colony-forming algae is an alga in a phylum selected from Zygnemataceae, Cladophoraceae, Oeologoniales, or a combination thereof.
5. The process of claim 4, wherein the starch-accumulating filament-forming or colony-forming algae is an alga selected from spirogyra, cladophora, oedogonium, or a combination thereof.
6. The process of claim 5, wherein the starch-accumulating filament-forming or colony-forming algae is spirogyra.
7. The process of claim 5, wherein the starch-accumulating filament-forming or colony-forming algae is cladophora.
8. The process of claim 5, wherein the starch-accumulating filament-forming or colony-forming algae is oedogonium.
9. The process of claim 1, wherein the growing forms an algal bloom.
10. The process of claim 1, wherein animal waste is used as a phosphate source in the aqua culture.
11. The process of claim 10, wherein the animal waste is selected from hog waste and poultry waste.
12. The process of claim 1, wherein the aqua culture is open to atmospheric conditions.
13. The process of claim 1, wherein the carbon dioxide level in the aqua culture is raised above atmospheric levels by the external addition of carbon dioxide.
14. The process of claim 1, wherein the yeast is selected from Saccharomyces cerevisiae and Saccharomyces uvarum.
15. The process of claim 1, wherein the yeast is Saccharomyces cerevisiae.
16. The process of claim 1, wherein the yeast is Saccharomyces uvarum.
17. The process of claim 1, wherein the separating is started once the level of ethanol in the fermentation solution is 12-17% by volume.
18. The process of claim 1, further comprising:
   (f) collecting the carbon dioxide generated during fermentation.
19. The process of claim 16, further comprising:
   (g) supplying the collected the carbon dioxide to the aqua culture.
20. The process of claim 1, further comprising:
   (h) isolating the lipids/oils present in the biomass after separation of the ethanol.
21. The process of claim 18, further comprising:
   (i) converting the isolated lipids/oils present into biodiesel.
22. A process for forming ethanol from algae, comprising:
   (a) harvesting a natural bloom of starch-accumulating, filament-forming or colony-forming algae to form a biomass;
   (b) harvesting the grown algae to form a biomass;
   (c) initiating decay of the biomass;
   (d) contacting the decaying biomass with a yeast capable of fermenting it to form a fermentation solution; and, separating the resulting ethanol from the fermentation solution.

* * * * *